United States Patent
Ikefuji et al.

(10) Patent No.: US 9,609,231 B2
(45) Date of Patent: Mar. 28, 2017

(54) IMAGING SYSTEM AND IMAGING METHOD

(71) Applicant: DAINIPPON SCREEN MFG. CO., LTD., Kyoto (JP)

(72) Inventors: Kunio Ikefuji, Kyoto (JP); Jiro Tsumura, Kyoto (JP); Yoshihiro Kurimura, Kyoto (JP)

(73) Assignee: SCREEN Holdings Co. Ltd. (JP)

( * ) Notice: Subject to any disclaimer, the term of this patent is extended or adjusted under 35 U.S.C. 154(b) by 76 days.

(21) Appl. No.: 14/459,737

(22) Filed: Aug. 14, 2014

(65) Prior Publication Data

US 2015/0070531 A1    Mar. 12, 2015

(30) Foreign Application Priority Data

Sep. 10, 2013    (JP) ................................. 2013-187116

(51) Int. Cl.
| | | |
|---|---|---|
| H04N 5/235 | (2006.01) | |
| G06T 5/00 | (2006.01) | |
| G01N 21/25 | (2006.01) | |
| H04N 5/232 | (2006.01) | |
| G01N 21/17 | (2006.01) | |

(52) U.S. Cl.
CPC ......... H04N 5/2355 (2013.01); G01N 21/253 (2013.01); G06T 5/009 (2013.01); H04N 5/23212 (2013.01); H04N 5/23245 (2013.01); G01N 2021/1772 (2013.01); G06T 2207/30024 (2013.01)

(58) Field of Classification Search
CPC ............. H04N 5/2355; H04N 5/23245; H04N 5/23212; G06T 7/0012; G06T 2207/30024; G01N 21/253; G01N 2021/1772; G01N 21/01; A61L 2/10; G06K 9/00127
See application file for complete search history.

(56) References Cited

U.S. PATENT DOCUMENTS

| | | | |
|---|---|---|---|
| 6,111,980 A * | 8/2000 | Sano ..................... | H04N 5/2353 348/223.1 |
| 6,462,771 B1 * | 10/2002 | Kitagawa ............. | G02B 21/365 348/74 |
| 6,724,461 B1 | 4/2004 | Yamazaki ........................ | 355/40 |

(Continued)

FOREIGN PATENT DOCUMENTS

| | | |
|---|---|---|
| JP | 63-290945 | 11/1988 |
| JP | 11-113562 | 4/1999 |

(Continued)

OTHER PUBLICATIONS

Office Action issued May 26, 2015 in corresponding Japanese Patent Application No. 2013-187116.

*Primary Examiner* — Luong T Nguyen

(74) *Attorney, Agent, or Firm* — Ostrolenk Faber LLP

(57) ABSTRACT

An imaging system 100 for imaging a sample in a medium carried in a container WP as an imaging object comprises: an imager 21 which obtains an original image by imaging the imaging object; and a data processor 33 which generates multi-gradation image data by performing a gradation correction on the original image, wherein the data processor 33 associates a luminance value corresponding to a luminance of the medium in the original image with a maximum gradation value in the gradation correction.

9 Claims, 10 Drawing Sheets

(56) References Cited

U.S. PATENT DOCUMENTS

| | | | |
|---|---|---|---|
| 2003/0043410 A1 | 3/2003 | Fukawa et al. | 358/2.1 |
| 2005/0116029 A1* | 6/2005 | Miki | G06Q 20/341 |
| | | | 235/380 |
| 2006/0039604 A1 | 2/2006 | Fukawa et al. | 382/168 |
| 2006/0227320 A1 | 10/2006 | Tamiya et al. | 356/300 |
| 2008/0170754 A1 | 7/2008 | Kawasaki | 382/104 |
| 2010/0034458 A1* | 2/2010 | Tada | G06T 5/007 |
| | | | 382/167 |
| 2012/0057044 A1* | 3/2012 | Shimizu | H04N 9/735 |
| | | | 348/223.1 |

FOREIGN PATENT DOCUMENTS

| | | |
|---|---|---|
| JP | 11-346313 | 12/1999 |
| JP | 2003-209693 | 7/2003 |
| JP | 2008-170283 | 7/2008 |
| JP | 2012-015704 | * 1/2012 |
| WO | WO 2004/086010 | 10/2004 |

* cited by examiner

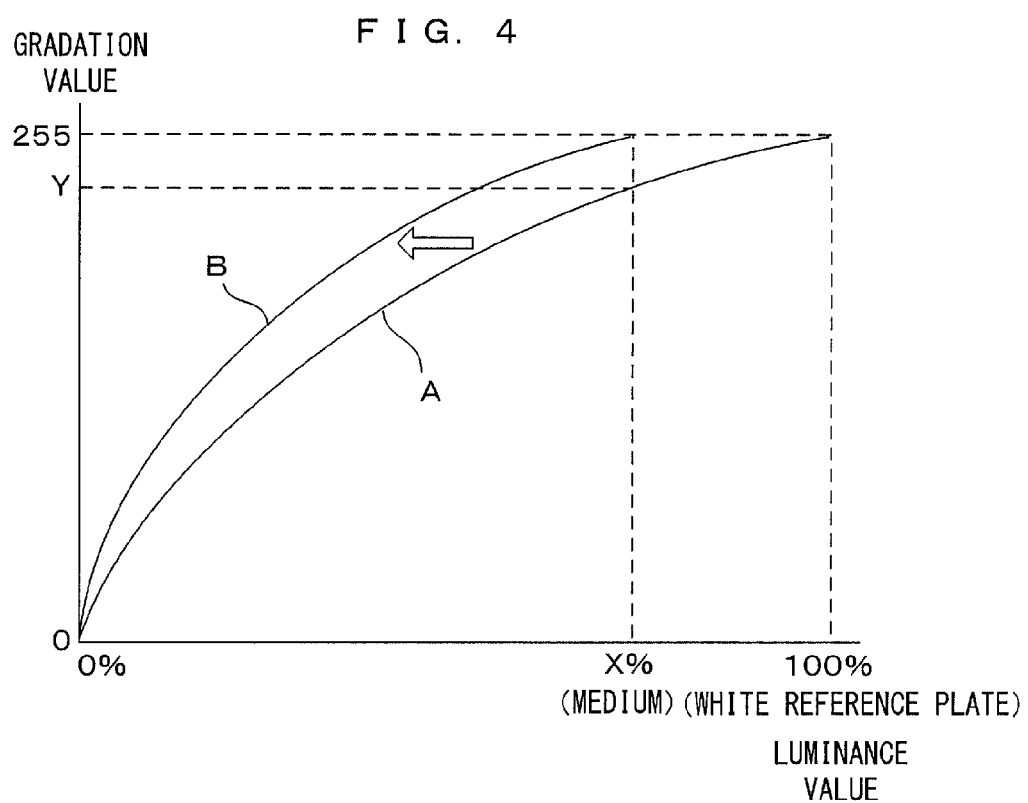

F I G. 8

| LUT NUMBER | TYPE OF MEDIUM | DENSITY OF MEDIUM | POURING AMOUNT | TYPE OF PLATE |
|---|---|---|---|---|
| 1 | TYPE 1 | 80% | 100 μl | TYPE A |
| 2 | TYPE 1 | 80% | 50 μl | TYPE B |
| 3 | TYPE 1 | 40% | 100 μl | TYPE A |
| 4 | TYPE 1 | 40% | 50 μl | TYPE B |
| 5 | TYPE 2 | 80% | 100 μl | TYPE C |
| 6 | TYPE 2 | 80% | 50 μl | TYPE D |
| 7 | TYPE 2 | 40% | 100 μl | TYPE A |
| 8 | TYPE 2 | 40% | 50 μl | TYPE B |
| 9 | TYPE 3 | 80% | 100 μl | TYPE A |
| 10 | TYPE 3 | 80% | 50 μl | TYPE B |
| 11 | TYPE 3 | 40% | 100 μl | TYPE C |
| 12 | TYPE 3 | 40% | 50 μl | TYPE D |

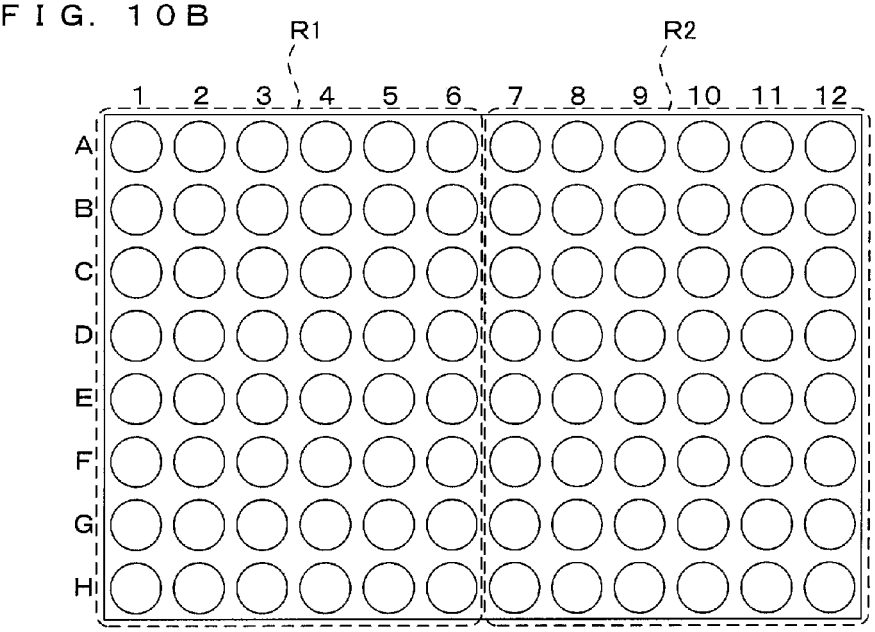

IMAGING SYSTEM AND IMAGING METHOD

CROSS REFERENCE TO RELATED APPLICATION

The disclosure of Japanese Patent Application No. 2013-187116 filed on Sep. 10, 2013 including specification, drawings and claims is incorporated herein by reference in its entirety.

BACKGROUND OF THE INVENTION

1. Field of the Invention

This invention relates to an imaging system and an imaging method for imaging a sample in a medium carried in a container as an imaging object.

2. Description of the Related Art

In medical and bio-scientific experiments, liquid or gel-like fluid (e.g. culture solution, medium or the like) is poured into each well of a plate-like tool (e.g. called microplate, microtiter plate or the like) in which a multitude of recesses also called as wells are, for example, arrayed, and things cultured herein such as cells are observed and measured as samples. In recent years, samples have been imaged and digitized by a CCD camera or the like and various image analysis techniques have been applied to image data for observation and analysis.

In an imaging system of this type, a correlation between actual optical densities of imaging objects and gradation values obtained by expressing the optical densities by multi-gradation image data is not necessarily linear due to non-linearity in the sensitivity of an, imaging system. Thus, a gradation correction (also called as a gamma correction or a tone correction) to properly adjust this is necessary. A technique applied to a document scanner for optically reading a plane document is known as a precedent of such a gradation correction technique. For example, in an image processing apparatus described in JP2003-209693A, pre-scanning is performed with a low resolution prior to actual scanning in scanning and reading a document image. A correction characteristic for a gradation correction, specifically a correlation between input gradation values and output gradation values is obtained from a histogram distribution characteristic of an obtained image and a gradation correction processing is performed during actual scanning.

It is considered to apply a gradation correction technique like the conventional technique also to an imaging system used for the purpose of observing samples such as cells. If imaging objects are samples in a culture medium, the medium is not perfectly transparent and has an optical density of a certain degree. Thus, there is a characteristic that a luminance of each pixel of an imaged image is not higher than a luminance corresponding to the medium itself. However, such a problem is naturally not considered in the above conventional technique aiming to read a document and only a correlation between luminance values and gradation values at intermediate gradations is focused. Thus, if this conventional technique is directly applied to the imaging of biological samples, gradation values are assigned up to a luminance level which is not applicable in an actual image, wherefore there has been a problem that a range of invalid gradation values not used in the multi-gradation expression of an image is created and a dynamic range of density expression in a multi-gradation image data is limited.

SUMMARY OF THE INVENTION

This invention was developed in view of the above problem and aims to provide a technique capable of generating multi-gradation image data representing an image obtained by imaging a sample in a medium in a wide dynamic range.

An imaging system for imaging a sample in a medium carried in a container as an imaging object according to the present invention comprises: an imager which obtains an original image by imaging the imaging object; and a data processor which generates multi-gradation image data by performing a gradation correction on the original image, wherein the data processor associates a luminance value corresponding to a luminance of the medium in the original image with a maximum gradation value in the gradation correction.

An imaging method for imaging a sample in a medium carried in a container as an imaging object according to the present invention comprises: an imaging step of obtaining an original image by imaging the imaging object; and a data processing step of generating multi-gradation image data by performing a gradation correction on the original image, wherein the multi-gradation image data is generated so that a luminance value corresponding to a luminance of the medium in the original image is associated with a maximum gradation value in the gradation correction of the data processing step.

In these inventions, in view of the above characteristic in the case of imaging the sample in the medium as the imaging object, the multi-gradation image data is generated based on a relationship between the luminance values and the gradation values associated such that the luminance value corresponding to the luminance of the medium provides the maximum gradation value. That is, the luminance values and the gradation values are associated in a luminance range having the luminance of the medium as an upper limit, and the original image is expressed in the form of the multi-gradation image data based on that. Thus, the gradation values are assigned according to the luminance range of an actual image of the imaging object and the image can be expressed in multiple gradations effectively using a dynamic range of the gradation values.

According to the present invention, the gradation correction processing is performed with the luminance values and the gradation values associated such that the luminance value corresponding to the luminance of the medium provides the maximum gradation value. Thus, multi-gradation image data representing an image obtained by imaging a biological sample in a medium in a wide dynamic range can be obtained by preventing the creation of a range of invalid gradation values.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

BRIEF DESCRIPTION OF THE DRAWINGS

FIG. 4 is a graph illustrating the scaling of the gradation correction characteristic.

FIG. 8 is a diagram showing an example of the reference table.

FIGS. 10A and 10B are views showing an arrangement example of samples on the well plate.

DETAILED DESCRIPTION OF THE PREFERRED EMBODIMENT

Figure 1:
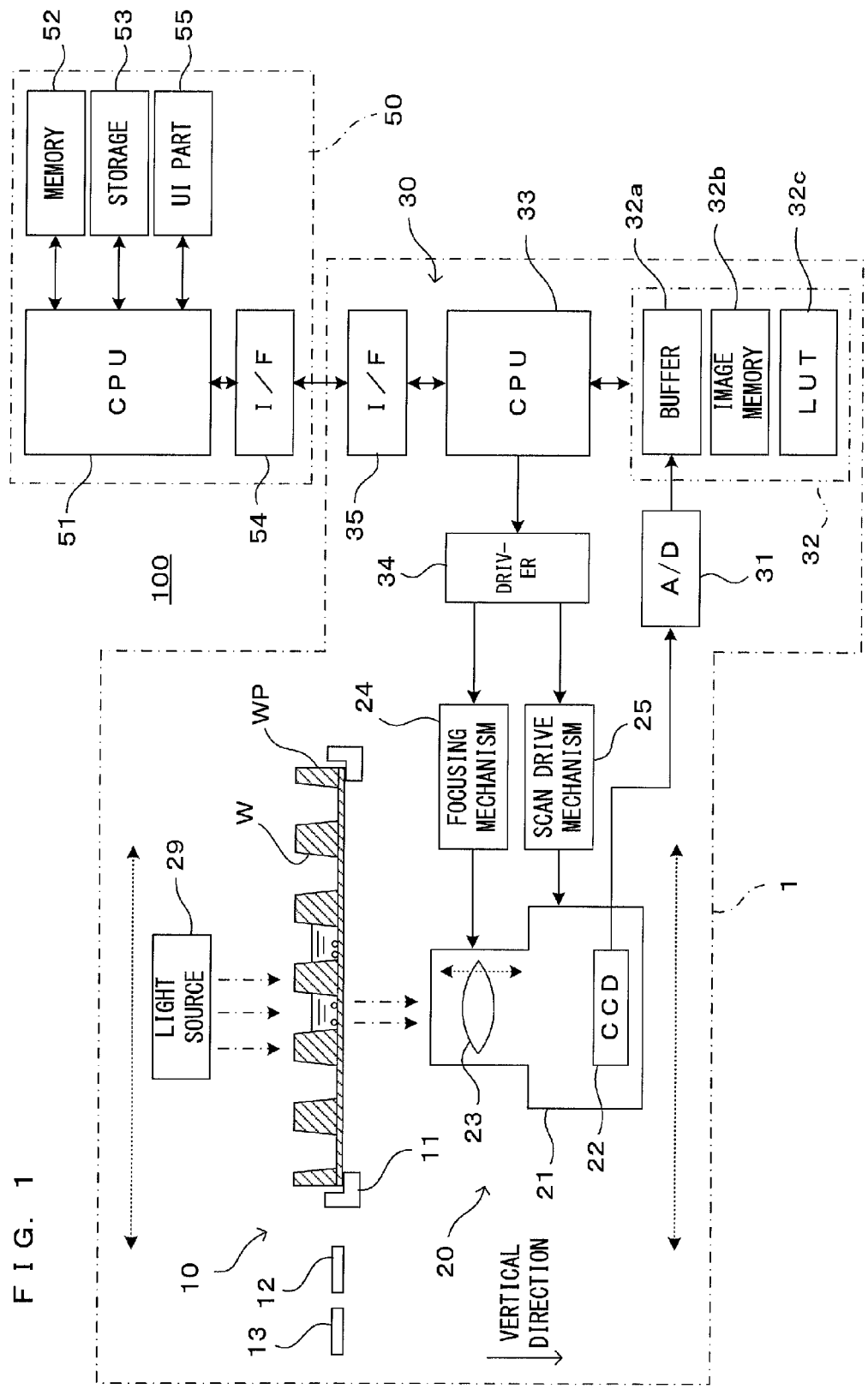
FIG. 1 is a view diagrammatically showing the configuration of one embodiment of an imaging system according to the invention.

FIG. 1 is a view diagrammatically showing the configuration of one embodiment of an imaging system according to the invention. This imaging system 100 is a so-called line CCD scanner apparatus using a CCD line sensor as an imaging device and includes an imaging unit 1 with a sample holder part 10, an optical scanner part 20 and a control part 30, and a host computer 50.

The sample holder part 10 includes a holder 11 for holding a well plate WP substantially in a horizontal posture by being held in contact with a peripheral edge part of the lower surface of the well plate WP. Wells W for carrying a culture medium containing biological samples such as cells as imaging objects are formed on the upper surface of the well plate WP. Further, the sample holder part 10 includes a white reference plate 12 and an AF reference plate 13 to be read as references in a shading correction processing and an autofocus (AF) adjustment processing respectively to be described later.

The well plate WP includes a plurality of, e.g. ninety six (12×8 matrix array) wells W each having a substantially circular cross-section and capable of carrying a liquid or solid medium. A diameter and a depth of each well W are typically about several millimeters. Note that the size of the well plate and the number of the wells for this imaging system 100 are not limited to these, and are arbitrary. For example, there may be 384 wells.

When the well plate WP is placed on the holder 11 in a state where the culture medium containing the samples is held in these wells W, light (e.g. white light) is irradiated to the well plate WP from a light source 29. The light source 29 is, for example, an LED lamp and arranged above the well plate WP held on the holder 11.

The optical scanner part 20 functions as an imager for optically imaging the imaging objects by receiving transmitted light from the imaging objects. The optical scanner part 20 includes an imaging part 21 in which CCD elements 22 as light receiving elements and a convergent optical system 23 for adjusting a magnification of an optical image by transmitted light are arranged below the well plate WP, a focusing mechanism 24 for focusing the convergent optical system 23, and a scan drive mechanism 25 for driving the imaging part 21 in a predetermined direction (lateral direction in FIG. 1), for example, by belt drive.

Out of the light irradiated toward the well plate WP from the light source 29, light transmitted downward from the bottom surface of the well W is converged by the convergent optical system 23 and received by the CCD elements 22, whereby an optical image is converted into electrical signals. The focusing mechanism 24 drives the convergent optical system 23 in response to a control command from the control part 30, thereby adjusting a focus position of the optical image focused on the CCD elements 22. Further, the scan drive mechanism 25 moves the light source 29 and the imaging part 21 integrally in a horizontal plane. Thus, a positional relationship between the light source 29 and the imaging part 21 is fixed.

Scanning movements of the CCD elements 22 relative to the well plate WP are realized by moving the CCD elements 22, which constitute a line sensor, in a direction perpendicular to an arrangement direction of the CCD elements 22 relative to the well plate WP. In this way, a two-dimensional image of the biological samples as the content of the well W is imaged. The optical scanner part 20 is controlled by the control part 30.

The control part 30 includes an A/D converter 31, a memory 32, a CPU 33 and a driver 34. The A/D converter 31 converts electrical signals output from the CCD elements 22 into luminance values (color density values) according to the received amounts of the transmitted light from the samples in the well W. The memory 32 holds a collection of the luminance values of respective pixels obtained from the samples as image data and stores various setting data. The CPU 33 functions as a controller for controlling each component of the apparatus. Further, the driver 34 drives the focusing mechanism 24 and the scan drive mechanism 25 in response to a control command from the CPU 33. The memory 32 is composed of a ROM, a RAM or a nonvolatile memory and the like, and includes a buffer memory 32a for temporarily holding luminance value data output from the A/D converter 31 and an image memory 32b for holding multi-gradation image data generated based on the luminance value data. Besides these, various pieces of reference data such as a reference table (LUT) 32c to be referred to in performing a gradation correction processing to be described later is stored in the memory 32 in advance.

The control part 30 thus configured can communicate with the host computer 50 for controlling the operation of the entire imaging system 100 via an interface part (I/F) 35. Specifically, the host computer 50 is configured similarly to a general personal computer and includes a CPU 51 for performing various arithmetic processings, a memory 52 for temporarily saving control data generated by the operation of the CPU 51, a storage 53 storing a control program to be executed by the CPU 51, an interface part (I/F) 54 for data transfer to and from the control part 30.

The host computer 50 also includes a user interface (UI) part 55 for receiving the input of various operations from a user and presenting various pieces of information to the user. More specifically, the UI part 55 includes at least one type of an input device such as operation buttons, a keyboard, a mouse or a touch panel as a receiver for receiving operational inputs from the user. Further, the UI part 55 includes a display for displaying, for example, obtained images, messages and the like on a screen.

Functions of receiving the input of various operations from the user to operate the imaging system 100 and presenting images obtained as a result of operations to the user are consolidated into the host computer 50. Accordingly, the control part 30 has only a minimum configuration for causing the optical scanner part 20 to perform a predetermined operation. As just described, the control part 30 having control functions minimum necessary to operate particular hardware is provided in this apparatus, whereas more general processings are performed by the versatile host computer 50, whereby system cost can be suppressed low.

Note that this imaging system 100 is composed of the imaging unit 1 integrally configured by the sample holder part 10, the optical scanner part 20 and the control part 30, and the general-purpose host computer 50 for controlling this imaging unit 1 as described above. Instead of this, all components necessary for imaging may be integrally incorporated. In the case of an imaging system composed of an imaging part and a host computer, hardware and software resources for storing image data and performing various analysis processings can be consolidated into the host computer. Since this makes it sufficient to include only hardware and software minimum necessary for imaging in the imaging unit, system cost can be suppressed.

Next, the operation of the imaging system 100 configured as described above is described. When receiving an instruction to start an imaging operation, i.e. an operation of reading the samples held in the sample holder part 10 from the user, this imaging system 100 images samples by performing a reading operation under designated conditions. Image signals generated by the CCD elements 22 of the imaging part 21 by the reading are converted into multi-gradation original image data by the A/D converter 31 of the control part 30. Original image data at this time is affected by a nonlinear sensitivity characteristic of the imaging system. Thus, this imaging system 100 performs a gradation correction processing for the original image data to generate multi-gradation image data having such nonlinearity removed. The following data processings are performed for each of color-separated color components in a system for imaging a color image.

Figure 2A:
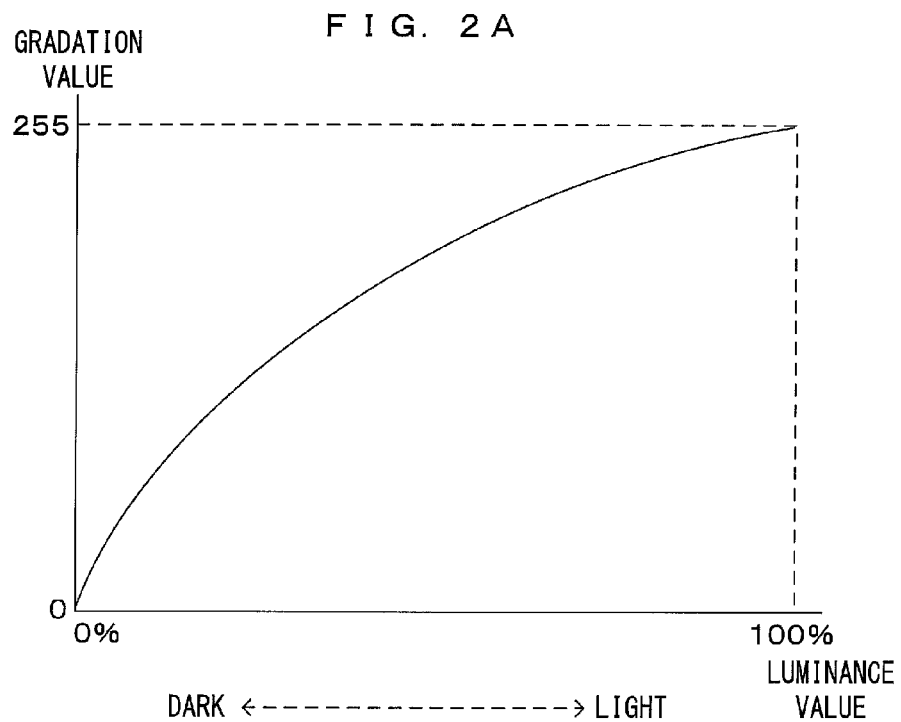
FIGS. 2A and 2B are a graph and a view outlining the gradation correction processing.
Figure 2B:
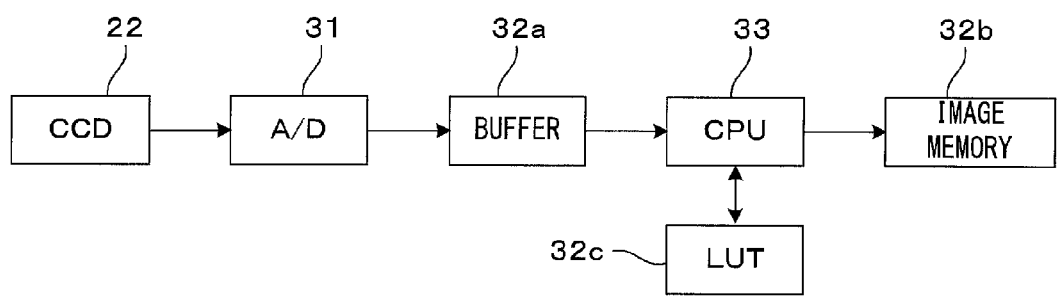

FIGS. 2A and 2B are a graph and a view outlining the gradation correction processing. More specifically, FIG. 2A is a graph showing an example of a gradation correction characteristic and FIG. 2B is a view diagrammatically showing a data flow of the gradation correction processing in this imaging system 100. In the case of expressing multi-gradation image data, for example, by 8-bit data, the number of gradations is 256 and a gradation value takes a value of 0 to 255 as shown in FIG. 2A. Light with highest luminance received by the CCD elements 22 is expressed by a luminance value of 100%, a zero light quantity is expressed by a luminance value of 0%, and a gradation value of 0 and a gradation value of 255 are respectively assigned to the luminance value of 0% and the luminance value of 100%. As shown in FIG. 2A, nonlinearity in the sensitivity of the imaging system is compensated by providing a linear correlation between the luminance values and the gradation values, whereby multi-gradation image data truer to an optical characteristic of imaging objects is obtained.

In this imaging system 100, such a correlation between the luminance values and the gradation values is digitized and stored as the look-up table (LUT) 32*c* in advance. As shown in FIG. 2B, analog image signals output from the CCD elements 22 are converted into digital data (original image data) by the A/D converter 31 and temporarily saved in the buffer 32*a*. Then, the CPU 33 refers to the LUT 32*c* based on the original image data output from the buffer 32*a*, converts the original image data into multi-gradation data having nonlinearity in the sensitivity of the imaging system corrected and stores the multi-gradation data in the image memory 32*b*. In this way, the gradation correction processing is performed.

Here, a data length of the multi-gradation image data finally stored in the image memory 32*b* is eight bits. On the other hand, the original image data handled by the A/D converter 31 and the buffer 32*a* has a longer bit length, e.g. twelve to sixteen bits. Further, an effective bit length in computations in the CPU 33 is sufficiently longer than eight bits. In such a configuration, the degradation of image quality can be prevented by suppressing the generation of noise in a process for generating multi-gradation image data from image signals.

Further, the image signals output from the CCD elements 22 are successively converted into digital data and saved in the image memory 32*b* after the gradation correction processing is performed thereon. That is, the original image data output from the A/D converter 31 is only temporarily saved in the buffer 32*a* for the correction processing, and the original image data corresponding to the entire image of one well plate WP or one well W is not saved. Thus, the image memory 32*b* has only to have a function and a capacity to save only 8-bit data after the gradation correction and the buffer 32*a* may have a small capacity.

Note that the buffer 32*a* is described as an independent function block to show the flow of the process in this specification, the buffer 32*a* can be realized, for example, by utilizing an internal buffer of a CPU or a part of a memory space of an image memory as a buffer area in an actual apparatus. For example, if image data after the gradation correction is transferred to the host computer 50 and stored in the host computer 50, a capacity of the image memory necessary in the imaging unit 1 can be largely reduced.

Next, how to set a light quantity equivalent to the luminance value of 100% in the original image data is described. In an imaging apparatus of this type, a shading correction of obtaining a shading characteristic by imaging a reference surface with a known optical characteristic and normalizing an incident light quantity based on this characteristic is generally performed to correct a sensitivity variation of an imaging device. Although specific processing contents are described in detail later, a shading correction processing is performed based on an imaging result of the white reference plate 12 having a predetermined transmittance also in this imaging system 100. Since there are various known techniques for the shading correction processing and a technique appropriately selected therefrom can be applied also to this imaging system 100, detailed description is not given here.

However, apparatuses for imaging samples such as cells carried together with a culture medium in the wells W of the well plate WP like this imaging system 100 have the following characteristics specific to such imaging.

Figure 3A:
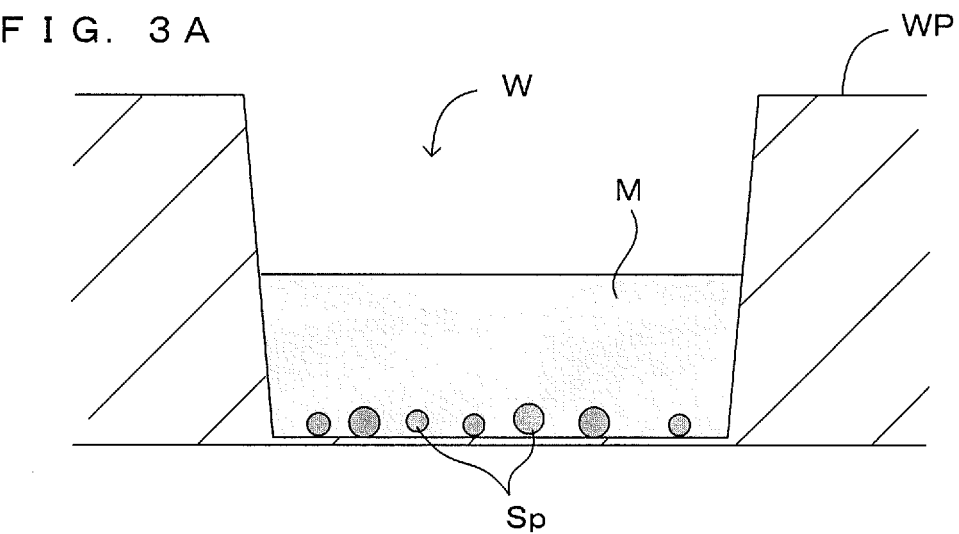
FIGS. 3A and 3B are views diagrammatically showing samples carried in the well plate.
Figure 3B:
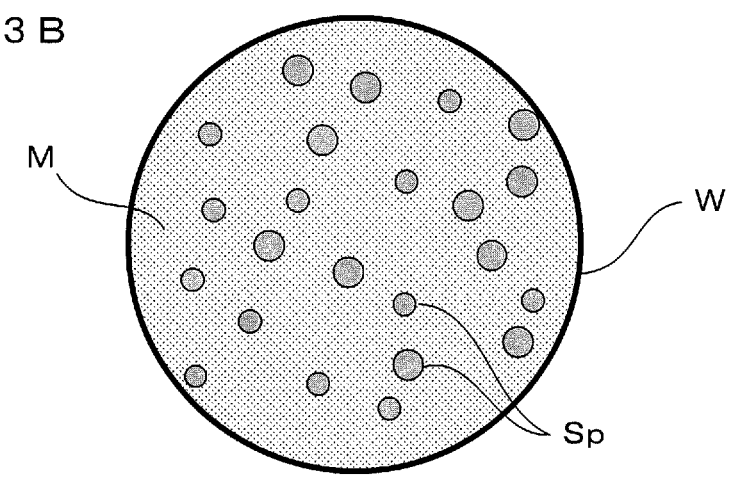

FIGS. 3A and 3B are views diagrammatically showing samples carried in the well plate. More specifically, FIG. 3A is a side sectional view of the well plate WP carrying a culture medium containing biological samples, and FIG. 3B is a bottom view of FIG. 3A. Imaging objects in this imaging system 100 are biological samples such as cell clusters (or spheroids) Sp present in the liquid, solid or gel-like medium (culture medium) M carried in the wells W provided in the well plate WP as shown in FIG. 3A. Here, although the cell clusters Sp distributed on the inner bottom surface of the well W are illustrated as an example, the imaging objects may be present on the surface or an intermediate part of the medium M. Further, the amount of the medium M (depth in the well W) also varies.

The medium M contains certain drug in many cases and is rarely a perfectly transparent body or white body. Accordingly, in the case of observing the imaging objects from below, the imaging objects such as the cell clusters Sp are generally distributed in the medium M having a certain optical density as shown in FIG. 3B. Thus, in an image obtained by imaging the interior of the well W, a luminance value of the medium M is highest and other parts have a lower luminance than this. That is, an actual image has a luminance distribution having the luminance value corresponding to the medium M as a maximum value.

On the other hand, since the luminance values are normalized based on the white reference plate 12 having a constant optical characteristic in the shading correction processing, a normalization result does not necessarily match a luminance distribution range of an actual image obtained by imaging the well W. Accordingly, in this imaging system 100, the gradation correction characteristic is scaled according to the luminance value of the medium M.

FIG. 4 is a graph illustrating the scaling of the gradation correction characteristic. The imaged light quantities (luminance values) are so normalized that the luminance value obtained by imaging the white reference plate 12 is 100% in the shading correction processing as shown by a curve A in FIG. 4. In the LUT 32c for the gradation correction processing, the maximum gradation value (255 in the case of eight bits) corresponds to the luminance value of 100% and the minimum gradation value of 0 corresponds to the luminance value of 0%.

On the other hand, in the actual image obtained by imaging the well W, the medium M has the highest luminance as described above. The shading correction processing is so performed that the luminance value is not higher than 100% regardless of samples imaged. The luminance value of the medium M varies depending on the type and state of the medium M. Accordingly, in many cases, the luminance value of the medium M is lower than 100%. If the luminance value of the medium M in the actual image is X % as shown in FIG. 4, multi-gradation image data corresponding to the actual image after the gradation correction is expressed in a range from 0 to a gradation value Y corresponding to the luminance value X and a numerical value range above the gradation value Y up to 255 is not used for the data representation of the image. That is, some of 256 gradations become invalid to narrow a dynamic range of multi-gradation expression.

Accordingly, in this embodiment, the gradation correction characteristic (curve A) associated with the gradation values in a luminance value range of 0% to 100% is scaled in a range from 0% to the luminance value X % of the medium M to obtain a corrected gradation correction characteristic (curve B) as shown by an arrow in FIG. 4. As a result, the gradation values from the minimum gradation value to the maximum gradation value are assigned in a luminance distribution range of the actual image. By applying the thus corrected gradation correction characteristic to perform the gradation correction processing, the actual image obtained by imaging the well W can be expressed in multiple gradations effectively using 256 gradations. This enables images to be expressed in a wider dynamic range.

Note that data stored in the LUT 32c preferably has a bit length longer than eight bits to prevent a reduction in computation accuracy caused by bit drop-out at the time of scaling. Further, a slight margin may be provided on a high gradation side in the assignment between the luminance values and the gradation values. Specifically, instead of assigning the maximum gradation value of 255 to the luminance value of the medium M, a slightly smaller gradation value (e.g. 250) may be assigned. By doing so, even a case where there is an area having a higher luminance than the medium or there is an error in calculating the luminance value of the medium can also be dealt with. In the following description, curves representing the gradation correction characteristic like the curves A, B shown in FIG. 4 may be referred to as "tone curves".

Next, two modes of an operation of imaging biological samples by this imaging system 100 using the above scaling of the gradation correction characteristic (tone curve) is described. In a first mode described below, the luminance value of the medium M is obtained by actually imaging given samples and the scaling is performed based on that value. On the other hand, in a second mode, the scaling is performed based on the luminance value of the medium M estimated from the type and state of the medium M. These two modes can be realized by using the same hardware configuration and making the operation of the hardware configuration partly different.

<First Mode>

Figure 5:
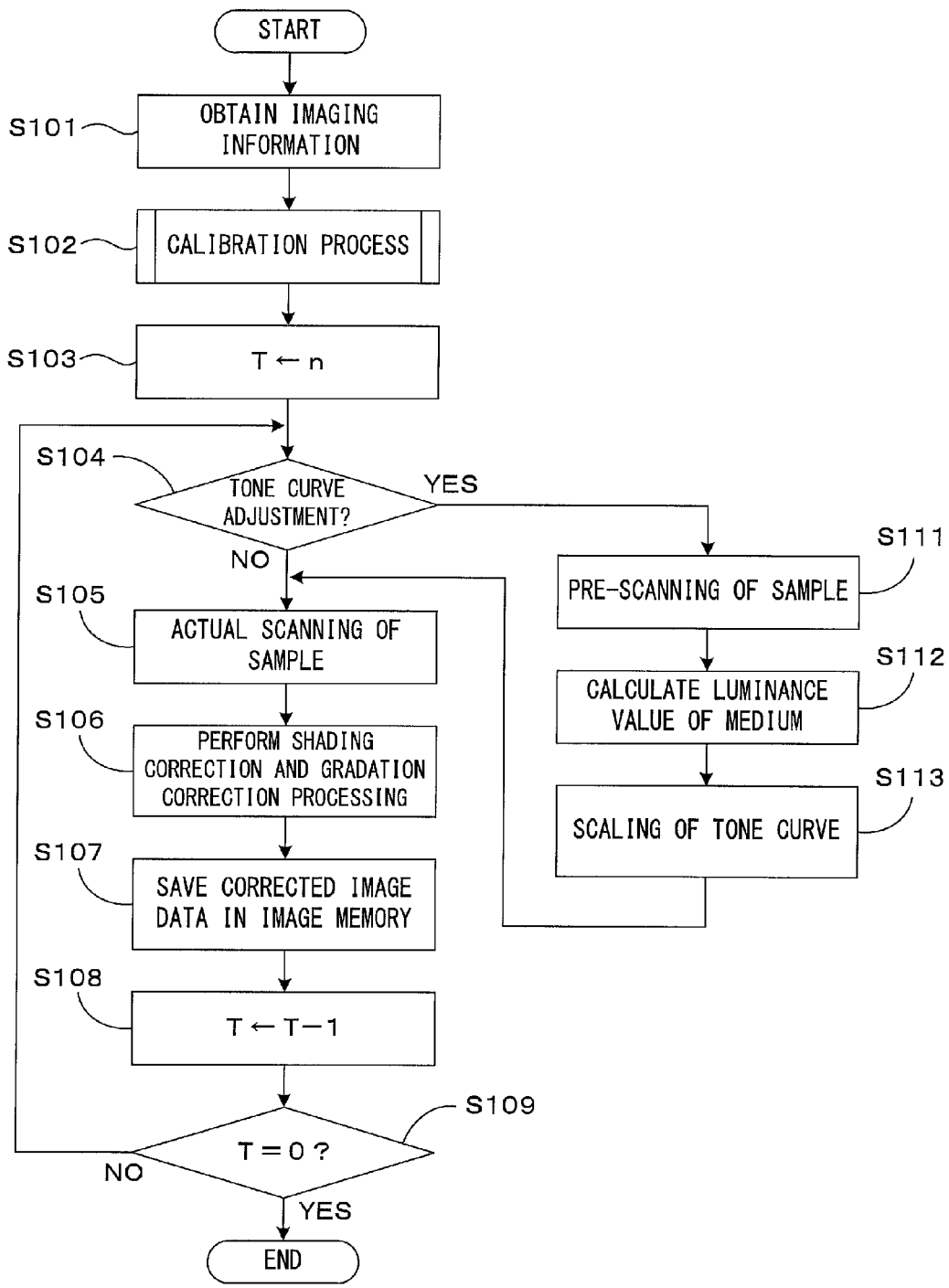
FIG. 5 is a flow chart showing the first mode of the imaging operation of this imaging system.
Figure 6:
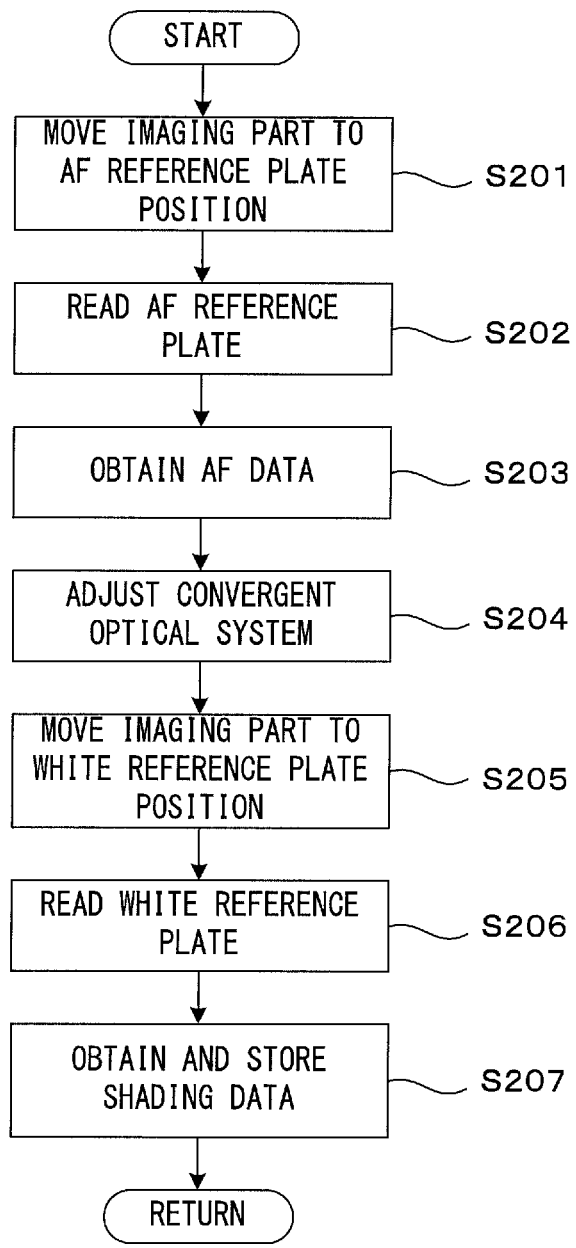
FIG. 6 is a flow chart showing the operation of a calibration process.

FIG. 5 is a flow chart showing the first mode of the imaging operation of this imaging system. Further, FIG. 6 is a flow chart showing the operation of a calibration process. These processes are realized by the CPU 33 executing the control program stored in the memory 32 in advance and causing each component of the apparatus to perform a predetermined operation.

When the host computer 50 receives an instruction input to the effect of starting the imaging operation from the user via the UI part 55, information (imaging information) designating the contents of the instruction and various imaging processings included in the user instruction is obtained by the control part 30 of the imaging unit 1 from the host computer 50 (Step S101). The imaging information includes, for example, the number and type of the well plate(s) WP to be imaged, the content of samples carried therein and imaging conditions (e.g. illumination condition, resolution). The imaging unit 1 having received this information performs the calibration process shown in FIG. 6 (Step S102).

The autofocus (AF) adjustment processing (Steps S201 to S204) and a processing for obtaining the shading characteristic (shading processing; Steps S205 to S207) are performed in the calibration process of this embodiment. Known techniques can be applied as the contents of these processings. Accordingly, the principles and detailed operations of these processings are not described here.

In the calibration process, the AF adjustment processing (Step S201 to S204) is first performed. Specifically, the scan drive mechanism 25 is actuated to move the imaging part 21 to a position right below the AF reference plate 13 (Step S201) and the optical scanner part 20 reads the AF reference plate 13 (Step S202). A predetermined reference line is drawn on the AF reference plate 13, an image of the reference line is obtained every time while a focus position of the convergent optical system 23 is changed and set in multiple stages by the focusing mechanism 24. The focus position where an image contrast of the reference line is maximized is set as an in-focus position and the setting of the convergent optical system 23 at that time is stored as AF data DA1 (Step S203) and the convergent optical system 23 is adjusted according to that setting (Step S204).

In this way, the in-focus position of the imaging part 21 is optimized. The samples are imaged in a state where the convergent optical system 23 is adjusted based on the AF data DA1 at this time until the autofocus adjustment processing is performed again.

Subsequently, the shading processing is performed (Steps S205 to S207). Specifically, the scan drive mechanism 25 is actuated to move the imaging part 21 to a position right below the white reference plate 12 (Step S205) and the optical scanner part 20 reads the white reference plate 12 (Step S206). The white reference plate 12 is a white flat plate having a predetermined light transmittance and transmits a part of light from the light source 29 positioned above the white reference plate 12 to allow it to be incident on the optical scanner part 20.

If V denotes a true color density value of the white reference plate 12 and an output value when the optical scanner part 20 reads the white reference plate 12 is shading data DS1, a relationship of:

$$DC = DD \times V/DS1 \quad \text{(Equation 1)}$$

holds for each pixel between read image data DD obtained by reading the samples and corrected image data DC after the shading correction.

The execution of the shading correction is nothing other than the obtainment of the corrected image data DC from the read image data DD based on the relationship of (Equation 1). In other words, by performing the shading processing to obtain the shading data DS1, a correction coefficient, i.e. a coefficient (V/DS1) on the right side of (Equation 1) when the shading correction is performed in the subsequent reading operations is obtained. Accordingly, this shading data DS1 is obtained from a reading result and stored (Step S207).

As just described, information necessary to perform the shading correction is obtained by performing the shading processing. As described later, the shading correction using the coefficient (V/DS1) obtained from the shading data DS1 at this time as a correction coefficient is performed until the shading processing is performed again.

Referring back to FIG. 5, a preparation for actually reading the samples is set when the calibration process is finished as described above. Subsequently, an internal parameter T indicating the number of the remaining well plates WP to be imaged is set to an initial value n designated as the imaging condition by the user (Step S103) and whether or not an adjustment of the tone curve is necessary is judged (Step S104). Here, the "adjustment of the tone curve" means a processing of scaling the tone curve stored in the LUT 32c according to the luminance value of the medium such as in the processing of obtaining the curve B by scaling the curve A shown in FIG. 4.

Whether or not the adjustment of the tone curve is necessary can be judged, for example, by the following criteria. First, if the samples to be imaged are new ones that have not been imaged thus far, the grasp of the luminance value of the medium M and an associated adjustment of the tone curve are necessary since the luminance value of the medium M is unknown.

On the other hand, if the samples as the imaging objects have been already imaged, it is, in principle, not necessary to adjust the tone curve. In an imaging system for imaging biological samples as imaging objects, so-called time-lapse imaging may be performed to regularly image the same samples at predetermined time intervals to observe changes in the samples with time. In this case, since comparative observation of images cannot be precisely performed if the imaging conditions change, imaging needs to be performed under the same imaging conditions. Thus, it is desirable to use the tone curve used in the previous imaging also in the later imaging and a re-adjustment of the tone curve is not necessary.

Note that even if the same samples are used, the color of the medium gradually changes with the passage of time and generally becomes gradually darker. Because of this, it is expected that the image contrast gradually decreases by continuing to apply the same tone curve. To deal with such a case, a configuration that can re-adjust the tone curve according to need may be adopted.

Also in the case of changing the imaging condition such as an intensity of illumination light, an imaging resolution or a scanning speed, the shading processing and the tone curve need to be adjusted.

Further, regardless of these requirements, if an instruction to the effect of making such adjustments or not making them is input by the user, that instruction is prioritized as a matter of course and whether or not the adjustment of the tone curve is necessary is judged.

If the adjustment of the tone curve is judged to be necessary, the pre-scanning of the samples and the adjustment of the tone curve based on this are subsequently performed (Steps S111 to S113). Specifically, the optical scanner part 20 operates for pre-scanning prior to actual scanning to image the well plate WP (Step S111) and the CPU 33 calculates the luminance value of an area corresponding to the medium in an obtained image of the well W (Step S112).

Since the imaging in this case is sufficient to be able to merely obtain the luminance value of the medium M and does not require a high resolution, the scanning speed may be set higher than normal or a scanning region may be limited. However, the shading correction processing based on the previously obtained shading data DS1 is performed on the imaged image.

As described above, since the luminance value of the medium M is thought to be highest even in an image including the cell clusters Sp and the like, a luminance value of an area with the highest luminance in the image can be simply regarded as the luminance value of the medium M. More precisely, it is, for example, possible to detect the cell clusters Sp and the like from the image by an image processing, set an area excluding areas taken up by them as an area corresponding to the medium and obtain a luminance value of that area. However, it is realistic to perform such a complicated processing in the host computer.

When the luminance value of the medium M is obtained in this way, the tone curve is scaled according to the luminance value of the medium M based on the principle shown in FIG. 4. Then, a new correlation between the luminance values of the original image before the correction and gradation values of the image after the correction is obtained (Step S113). The tone curve is adjusted in this way. This causes a correction characteristic applied to the later gradation correction processing to be determined.

Since the color of the medium carried in the well W differs if the type and amount thereof differ, the tone curve needs to be originally adjusted based on the luminance value of the medium M for each well W. However, since the luminance value is thought to be substantially equal if the type and amount of the medium and a preparation time thereof are the same, a common tone curve may be applied to each well W in such a case. Here, it is assumed that the medium of the same conditions is prepared in the entire well plate WP and a case of including different media is described later.

If the tone curve is adjusted or the adjustment is judged to be unnecessary in Step S104, actual scanning is subsequently performed for the samples (Step S105). Actual scanning is the scanning of the imaging part 21 to obtain an image of the samples and imaging is performed with a resolution and under imaging conditions designated by the user. When the original image data DD of each pixel is obtained by actual scanning, the shading correction based on (Equation 1) and the gradation correction processing based on the adjusted tone curve are performed pixel by pixel on the original image data DD, whereby image data expressing the original image in 256 gradations is obtained (Step S106).

This multi-gradation image data is saved in the image memory 32 (Step S107) and utilized in various image processing apparatuses and the like as an output of the imaging system 100.

When imaging is finished for one well plate WP in a manner as described above, the parameter T indicating the number of the remaining well plates WP is decremented by 1 (Step S108) and the processings in and after Step S104 are repeated until the value of the parameter T becomes 0 (Step S109). At this time, whether or not it is necessary to re-adjust the tone curve is judged based on whether or not the same medium as that in the previously imaged well plate WP is used, and Steps S111 to S113 are performed again if necessary.

Note that the tone curve applied to the imaging of each well plate WP is stored as imaging history information in the memory 52 or the storage 53 of the host computer 50 while being associated with information for identifying the well plate WP. As described above, the same processing conditions are desirably applied for the same samples and the information of the tone curve applied to each well plate WP can be used for this purpose by being stored. This information is given as the imaging information from the host computer 50 to the imaging unit 1 according to need when the imaging operation is performed.

<Second Mode>

Figure 7:
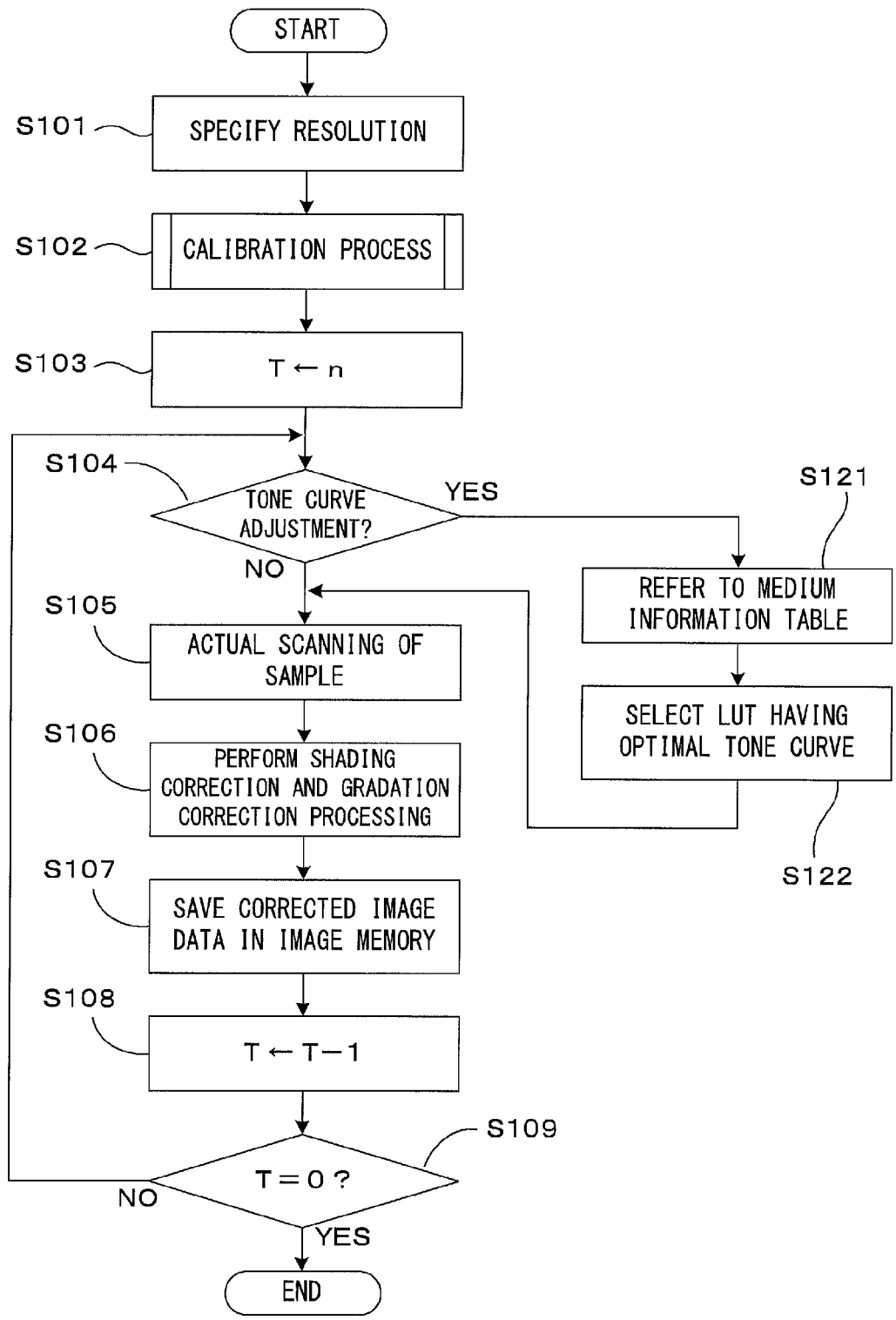
FIG. 7 is a flow chart showing the second mode of the imaging operation of this imaging system.

FIG. 7 is a flow chart showing the second mode of the imaging operation of this imaging system. In this mode, an operation of adjusting the tone curve differs, but the other operations are the same as in the first mode shown in FIG. 5. Accordingly, in FIG. 7, the same processings as those shown in FIG. 5 are denoted by the same reference signs and not described.

In this mode, if the adjustment of the tone curve is judged to be necessary in Step S104, a look-up table corresponding to the medium is selected from a plurality of look-up tables prepared in advance without performing the pre-scanning of the samples. Specifically, the plurality of look-up tables (LUTs) in which the tone curve represented by the curve A in FIG. 4 are scaled at different ratios are generated in advance and stored in the memory 32 of the imaging unit 1 or the memory 52 or the storage 53 of the host computer 50. If a data amount is large, these LUTs are preferably stored in the host computer 50.

Further, in the host computer 50, a reference table associating medium information representing the types and amounts of media and the LUTs corresponding to tone curves optimal for the media specified thereby is generated in advance in addition to the LUTs for gradation correction representing the tone curves, and stored in the memory 52 or the storage 53.

FIG. 8 is a diagram showing an example of the reference table. In this reference table 56, the type and the density of the medium, a pouring amount into the well W and the type of the well plate WP are input as the "medium information". Since a constant correlativity is thought to exist between the medium specified from these pieces of information and the luminance value of this medium, the luminance value of the medium can be estimated without actual measurement by using the medium information. If the luminance value of the medium can be estimated, the LUT corresponding thereto can be selected.

The medium information is preferably associated with a database used by the user to manage the samples. Specifically, it has been conventionally widely practiced to generate a database to be unitarily managed by the host computer 50 for the contents, preparation conditions and the like of various samples prepared by the user. If the medium information of the samples carried in the well plate WP is given to the imaging unit 1 from the database when the well plate WP desired to be imaged by the user is designated from this database, the user needs not designate the medium information at the time of imaging.

Further, in generating the reference table, it is, for example, considered to experimentally prepare media specified by the medium information in advance, image them to actually measure luminance values, select the LUTs most suitable for these media from the plurality of prepared LUTs for gradation correction and make them into a database. Further, the compilation of the reference table by the user may be enabled, so that data can be added and deleted.

In an example of FIG. 8, twelve LUTs (numbers of 1 to 12) are assigned one-to-one to twelve sets of the type and density of the medium, the pouring amount into the well W and the type of the well plate WP. If the medium information of the samples to be imaged is known, this reference table 56 is referred to (Step S121) and one LUT including the tone curve optimal therefor is selected (Step S122). In this way, as in the first mode, the tone curve is adjusted to the optimal one corresponding to the medium of the samples and applied to the gradation correction processing.

<Modification>

Note that although the medium information and the LUT number suitable therefor is associated in the reference table 56 shown in FIG. 8, a reference table associating the medium information and the luminance values of the media estimated therefrom may be provided instead of this. In this case, an estimated value of the luminance value of the medium is obtained as a result by referring to the reference table based on the medium information. The tone curve may be scaled using this estimated value instead of the actually measured luminance value of the medium M in the first mode and applied to the gradation correction processing.

<Miscellaneous>

Figure 9A:
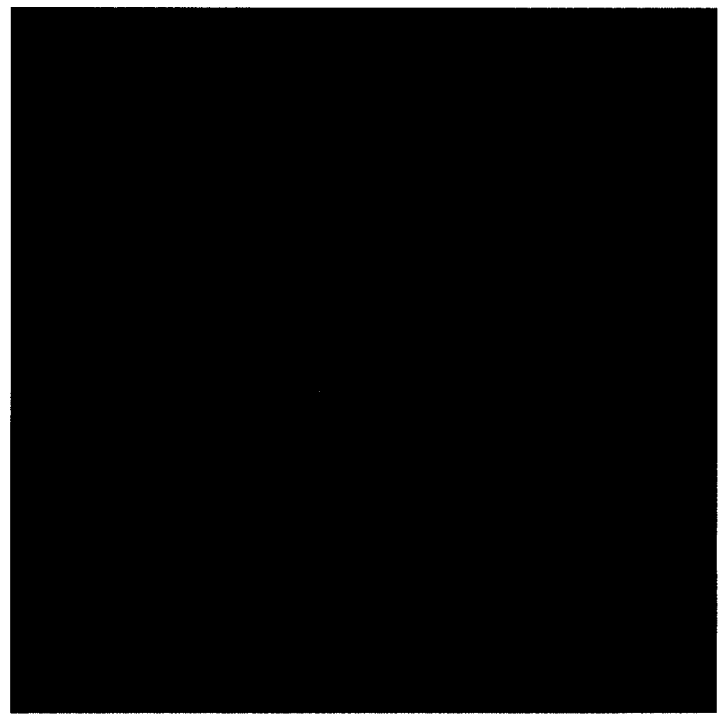
FIGS. 9A and 9B are views showing a difference between images due to the presence or absence of the adjustment of the tone curve.
Figure 9B:
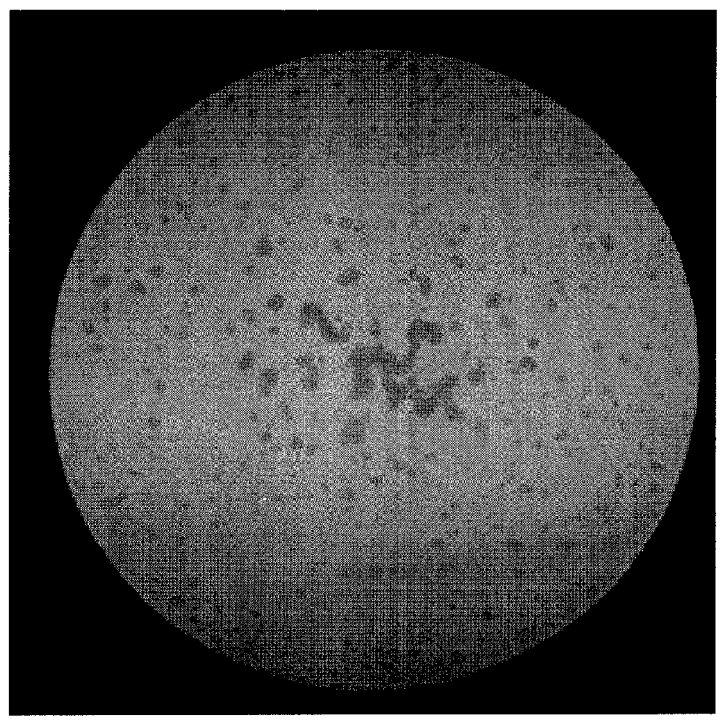

FIGS. 9A and 9B are views showing a difference between images due to the presence or absence of the adjustment of the tone curve. FIG. 9A shows an example of an image obtained by performing the shading correction processing and the gradation correction processing not associated with the scaling. FIG. 9B shows an example of an image obtained by performing the shading correction processing and the scaled gradation correction processing. Imaging objects are the same between these examples. Since the gradation correction processing of associating the luminance value of the white reference plate 12 with the maximum gradation value is performed in the example of FIG. 9A in which the scaling is not performed, a relative low gradation value is assigned to each pixel and the image is entirely dark and has a low contrast. On the other hand, since the maximum gradation value is assigned to the luminance value of the medium in the example of FIG. 9B in which the scaling is performed, the image is brighter and has a large density difference and a high contrast since the image is expressed in a wider dynamic range.

Next, a method for preparing samples suitable for imaging using this imaging system 100 is described. As described thus far, the tone curve is scaled according to the luminance value of the medium. Thus, if the medium differs in each well W, a different tone curve is applied to the gradation correction processing. However, since the original image data generated during imaging is successively subjected to the correction processing and deleted from the buffer 32a, the original image data needs to be obtained by individually operating the imaging part 21 to perform imaging for each well W having a different tone curve.

Since this prevents the extension of a time required for the imaging process, the samples using the same medium are desirably collected and arranged on the well plate WP.

FIGS. 10A and 10B are views showing an arrangement example of samples on the well plate. In this example is illustrated the well plate WP in which the wells W are arranged in a matrix in eight rows respectively assigned with row numbers of A to H and twelve columns respectively assigned with column numbers of 1 to 12. As shown in FIG. 10A, it is assumed that cells A are cultured in the wells in the first to third columns, cells A' are cultured in the wells in the fourth to sixth columns, cells B are cultured in the wells in the seventh to ninth columns and cells B' are cultured in the wells in the tenth to twelfth columns. On the other hand, compounds as drugs are added to the medium at a different concentration in each row. Note that the wells in the row indicated by the row number B are empty to prevent the mixing (contamination) of drug from the wells (having the row numbers C to H) containing drug to the wells (having the row number A) containing no drug. In such a well plate WP, sample groups 1 to 32 having different combinations of the cell types and the drug concentration are formed.

Since the samples are prepared under the same conditions in each group, a common tone curve can be applied. On the other hand, a different tone curve may be used for each group among different groups, but actual scanning by the imaging part 21 needs to be performed thirty two times in this case. If the medium is the same, the same tone curve can be applied. If a common medium is used in the groups 1 to 16 and another common medium is used in the groups 17 to 32, it is sufficient to perform actual scanning in a region R1 where the groups 1 to 16 are arranged and a region R2 where the groups 17 to 32 are arranged as shown in FIG. 10B. Thus, it is sufficient to perform actual scanning twice. As just described, the samples using the same medium are desirably collected as much as possible and arranged in the well plate WP to efficiently perform the scanning of the imaging part 21 a smaller number of times.

As described above, in this embodiment, multi-gradation image data is generated by performing the gradation correction processing in which the luminance value obtained in the medium is associated with the maximum gradation value in imaging the imaging objects (e.g. cell clusters Sp) carried in the well W of the well plate WP together with the medium M. By doing so, an image can be expressed in multiple gradations in a wide dynamic range effectively using the numeral value range of the gradation values and an image can be digitized with good image quality.

Specifically, the tone curve in which the luminances from the minimum luminance to the maximum luminance received by the CCD elements 22 are associated with the gradation values from the minimum gradation value to the maximum gradation value is stored in advance as the look-up table (LUT) and the tone curve is scaled according to the luminance value of the medium and applied to the gradation correction processing, whereby imaging in such a dynamic range is enabled.

In the first mode of the imaging operation of this imaging system 100, the luminance value of the medium is actually measured by the pre-scanning of the samples and the tone curve is scaled based on that value. Further, in the second mode, the optimal LUT is selected from the plurality of LUTs scaled in advance based on the luminance value estimated from the medium information specifying the medium. Since the gradation values are assigned in the luminance range corresponding to the luminance distribution of the original image corresponding to the samples in each of these modes, an image can be expressed in multiple gradations in a wide dynamic range.

The A/D converter 31 for converting the image imaged by the CCD elements 22 into digital data outputs original image data having a bit length longer than 8-bit data finally saved as the multi-gradation image data. Accordingly, the original image data has higher data resolution than the multi-gradation image data. The 8-bit data as the multi-gradation image data is generated by performing the gradation correction processing on the original image data. In such a configuration, the degradation of the image quality caused by the rounding of lower bits during computation can be prevented.

Further, in this imaging system 100, the shading correction processing based on the shading data DS1 obtained from the imaging result of the white reference plate 12 is performed together with the above gradation correction processing. A variation of the image quality due to a sensitivity variation of the imaging optical system can be suppressed by the shading correction process. Further, images with good image quality can be obtained by performing the aforementioned gradation correction processing to correct nonlinearity in the sensitivity of the imaging system in addition.

Further, in this imaging system 100, the information indicating which correction characteristic was applied in the gradation correction processing when the samples were imaged is stored as the imaging history information together with the information for specifying the samples. When the samples imaged in the past are imaged again, the gradation correction processing to which the gradation correction characteristic applied in the previous imaging, i.e. last imaging out of the imagings performed in the past is applied can be performed regardless of the luminance of the medium at that point of time. Since the correction processing is performed on a plurality of images of the same samples imaged at time intervals under the same processing conditions, images suitable for comparative observation between these images can be provided.

As described above, in this embodiment, the well plate WP corresponds to a "container" of the invention. Further, the CCD elements 22 of the imaging part 21 and the A/D converter 31 of the control part 30 integrally function as an "imager" of the invention, whereas the CPU 33 functions as a "data processor" of the invention. Further, the information stored in the form of the LUT 32c corresponds to "correction characteristic information" of the invention, and the memory 32 storing this functions as an "information holder" of the invention. Further, the reference table 56 corresponds to a "reference table" of the invention. Further, the white reference plate 12 functions as a "luminance reference member" of the invention.

Further, in the imaging operation (FIGS. 5 and 7) of this embodiment, Step S105 corresponds to an "imaging step" of the invention and Step S106 corresponds to a "data processing step" of the invention.

Note that the invention is not limited to the above embodiment and various changes other than the above ones can be made without departing from the gist thereof. For example, in the first mode of the imaging operation in the above embodiment, pre-scanning (Step S111) is performed before the actual scanning of the samples (Step S105) is performed, and the tone curve is scaled based on that result to determine the gradation correction characteristic. However, imaging for obtaining the luminance value of the medium may be performed after actual scanning. Further, even if the luminance value of the medium is obtained from an image obtained by actual scanning, a result similar to the above can be obtained from the perspective of optimizing the gradation correction characteristic. However, in these cases, the original image data obtained by actual scanning needs to be temporarily saved since the gradation correction characteristic is not determined at the time of actual scanning. Thus, a change of providing a large-capacity memory in the imaging unit 1 or causing the host computer 50 to perform the gradation correction processing or the like is necessary.

Further, the assignment of the functions to the host computer 50 and the imaging unit 1 in the above embodiment is an example and not limited to the above example. For example, the imaging unit may merely perform imaging, i.e. perform only an operation of scanning the samples and generating digital data, and all the other data processings may be performed by the host computer. Further, an integrated imaging system provided with all the above processing functions may be adopted.

Further, the imaging part 21 of the above embodiment obtains a two-dimensional image by scanning and moving the CCD elements 22 as a linear imaging device relative to the imaging objects. However, the imager of the invention may obtain a two-dimensional image, for example, by an area sensor fixedly positioned relative to imaging objects without being limited to the one obtained by such a scanning movement of a linear sensor.

Further, although the shading correction processing and the gradation correction processing are performed on the original image data imaged by the imaging part 21 in the above embodiment, the gradation correction processing according to the invention is also effective in cases not associated with the shading correction processing. Further, the shading correction processing may be performed on analog signals outputs from the CCD elements 22.

Further, although the calibration process (autofocus adjustment processing and shading processing) are performed after an imaging instruction from the user is received in the above embodiment, the calibration process may be automatically performed, for example, after the start of the system or regularly without depending on an instruction from the user. In such a case, since imaging can be immediately performed when an imaging instruction from the user is received, a waiting time of the user until imaging is finished can be shortened.

Further, in the above embodiment, the scanning movement of the imaging part 21 relative to the well plate WP is realized by fixing the well plate WP and moving the light source 29 and the imaging part 21 integrally relative to the well plate WP. However, a similar scanning movement can be realized also by a configuration for fixing the light source 29 and the imaging part 21 and moving the well plate WP, and the invention can be applied also to apparatuses having such a configuration. Further, although the light source 29 and the imaging part 21 are arranged at the opposite sides of the well plate WP carrying the imaging objects in the above embodiment, the invention can be applied to apparatuses in which the light source 29 and the imaging part 21 are arranged at the same side of the well plate WP and reflected light from the well plate WP is read. Further, the imaging objects are not limited to those carried in the well plate WP as a container and various other containers can be used as the "container" of the invention.

The invention can be particularly suitably applied in fields requiring the imaging of samples including, for example, biological bodies such as wells on a well plate used, for example, in the fields of medicine and bio-science, and fields of application thereof are not limited to medical and bio-scientific fields.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. An imaging system for imaging a sample in a medium carried in a container as an imaging object, comprising:
    an imager which obtains an original image by imaging the imaging object;
    a data processor which generates multi-gradation image data by performing a gradation correction on the original image,
    wherein the data processor associates a luminance value prepared in advance corresponding to the medium with a maximum gradation value in the gradation correction; and
    a reference table associating medium information including a type of the medium and a pouring amount into the container and the luminance of the medium specified by the medium information,
    wherein the luminance of the medium is obtained based on the medium information given by a user and the reference table.

2. The imaging system according to claim 1, further comprising an information holder which holds correction characteristic information associating luminance values from a minimum luminance to a maximum luminance and gradation values from a minimum gradation and a maximum gradation, wherein
    the data processor performs the gradation correction based on a scaled correction characteristic information which is obtained by scaling the correction characteristic information such that the luminance of the medium corresponds to the maximum luminance.

3. The imaging system according to claim 1, wherein:
    the imager outputs data having higher data resolution than the multi-gradation image data as original image data representing the original image; and
    the data processor performs the gradation correction on the original image data.

4. The imaging system according to claim 3, wherein a bit length of the original image data is longer than a bit length of the multi-gradation image data.

5. The imaging system according to claim 1, wherein the data processor performs a shading correction based on a shading characteristic obtained from an image of a predetermined luminance reference member imaged by the imager and the gradation correction on the original image.

6. An imaging method for imaging a sample in a medium carried in a container as an imaging object, comprising:
    an imaging step of obtaining an original image by imaging the imaging object;
    a data processing step of generating multi-gradation image data by performing a gradation correction on the original image,
    wherein the multi-gradation image data is generated so that a luminance value prepared in advance corresponding to the medium is associated with a maximum gradation value in the gradation correction of the data processing step; and an input step of receiving an input of medium information including a type of the medium and a pouring amount into the container from a user, wherein the luminance of the medium is obtained based on the medium information and a reference table associated with the luminance of the medium specified by the medium information.

7. The imaging method according to claim 6, wherein:

correction characteristic information associating luminance values of the original image from a minimum luminance to a maximum luminance and gradation values from a minimum gradation and a maximum gradation is generated in advance; and the gradation correction is performed based on a scaled correction characteristic information which is obtained by scaling the correction characteristic information such that the luminance of the medium corresponds to the maximum luminance.

8. The imaging method according to claim 6, further comprising a shading correction step of performing a shading correction on the original image based on a shading characteristic obtained from an image obtained by imaging a predetermined luminance reference member.

9. The imaging method according to claim 6, wherein a same gradation correction as the one applied in the last performed data processing step for the imaging object is applied in the data processing step performed again when the imaging step and the data processing step are performed again on the imaging object for which the imaging step and the data processing step were performed in the past.

* * * * *